US010035972B2

(12) United States Patent
Bedoukian et al.

(10) Patent No.: US 10,035,972 B2
(45) Date of Patent: *Jul. 31, 2018

(54) FRAGRANCE AND FLAVOR COMPOSITIONS CONTAINING ISOMERIC ALKADIENALS OR ISOMERIC ALKADIENENITRILES

(71) Applicant: BEDOUKIAN RESEARCH, INC., Danbury, CT (US)

(72) Inventors: Matthew Bedoukian, Redding, CT (US); Heidi A. Cristofalo, Redding, CT (US); Hifzur R. Ansari, Old Tappan, NJ (US)

(73) Assignee: Bedoukian Research, Inc., Danbury, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/372,888

(22) Filed: Dec. 8, 2016

(65) Prior Publication Data

US 2017/0166836 A1  Jun. 15, 2017

Related U.S. Application Data

(60) Provisional application No. 62/266,404, filed on Dec. 11, 2015.

(51) Int. Cl.
| | |
|---|---|
| *C11B 9/00* | (2006.01) |
| *A23C 9/156* | (2006.01) |
| *A23L 2/56* | (2006.01) |
| *A61K 8/33* | (2006.01) |
| *A61K 8/40* | (2006.01) |
| *A61Q 15/00* | (2006.01) |
| *A61Q 19/00* | (2006.01) |
| *C11D 3/50* | (2006.01) |
| *C11D 3/20* | (2006.01) |
| *C11D 3/26* | (2006.01) |
| *A23L 27/20* | (2016.01) |
| *A23L 27/24* | (2016.01) |
| *A23L 27/29* | (2016.01) |

(52) U.S. Cl.
CPC ............ *C11B 9/0023* (2013.01); *A23C 9/156* (2013.01); *A23L 2/56* (2013.01); *A23L 27/202* (2016.08); *A23L 27/25* (2016.08); *A23L 27/29* (2016.08); *A61K 8/33* (2013.01); *A61K 8/40* (2013.01); *A61Q 15/00* (2013.01); *A61Q 19/002* (2013.01); *C11B 9/0015* (2013.01); *C11D 3/2072* (2013.01); *C11D 3/26* (2013.01); *C11D 3/50* (2013.01)

(58) Field of Classification Search
CPC ........................................................ C11B 9/00
See application file for complete search history.

(56) References Cited

U.S. PATENT DOCUMENTS

| | | | |
|---|---|---|---|
| 3,686,003 A | 8/1972 | van Dorp et al. | |
| 3,821,421 A | 6/1974 | Begemann et al. | |
| 3,920,752 A | 11/1975 | Lamparsky | |
| 3,928,402 A | 12/1975 | Näf | |
| 4,105,697 A | 8/1978 | Chabardes | |
| 4,380,675 A | 4/1983 | Gebauer et al. | |
| 4,687,599 A | 8/1987 | Van Lier et al. | |
| 7,192,913 B2* | 3/2007 | Clark | A01N 3/00 512/1 |
| 7,989,013 B2 | 8/2011 | Chaintreau et al. | |
| 8,445,051 B2 | 5/2013 | Blandino et al. | |
| 2015/0164764 A1* | 6/2015 | Bonnet | A61K 8/602 514/777 |

OTHER PUBLICATIONS

Delort et al.; "Identification and Synthesis of New Volatile Molecules Found in Extract Obtained from Distinct Parts of Cooked Chicken", Journal of Agricultural and Food Chemistry, 2011, 59, 11752-11763.
Mosciano et al.; "Organoleptic Characteristics of Flavor Materials", Perfumer & Flavorist, 55, vol. 23, May/Jun. 1998, 3 pages.
International Search Report dated Apr. 20, 2017 from corresponding International Patent Application No. PCT/US2016/065573, 5 pages.
Written Opinion dated Apr. 20, 2017 from corresponding International Patent Application No. PCT/US2016/065573, 8 pages.

* cited by examiner

*Primary Examiner* — Arrie L Reuther
(74) *Attorney, Agent, or Firm* — Ohlandt, Greeley, Ruggiero & Perle, L.L.P.

(57) ABSTRACT

A composition containing at least one isomeric alkadienal or at least one isomeric alkadienenitrile in an amount effective to impart a fragrance or flavor to the composition. A fragrance or flavor composition containing at least one isomeric alkadienal or at least one isomeric alkadienenitrile in an amount effective to impart a fragrance or flavor to the composition. A consumer product containing the fragrance or flavor composition having at least one isomeric alkadienal or at least one isomeric alkadienenitrile in an amount effective to impart a fragrance or flavor to the composition. A method of imparting a fragrance or flavor to a consumer product by adding to the consumer product a fragrance or flavor composition containing at least one isomeric alkadienal or at least one isomeric alkadienenitrile in an amount effective to impart a fragrance or flavor to the consumer product.

19 Claims, No Drawings

FRAGRANCE AND FLAVOR COMPOSITIONS CONTAINING ISOMERIC ALKADIENALS OR ISOMERIC ALKADIENENITRILES

RELATED APPLICATION

This application claims the benefit of U.S. Application No. 62/266,404, filed Dec. 11, 2015, which is incorporated herein by reference in its entirety.

BACKGROUND OF THE DISCLOSURE

1. Field of the Disclosure

This disclosure relates to fragrance and flavor compositions containing isomeric alkadienals or isomeric alkadienenitriles. This disclosure also relates to a method of imparting a fragrance or flavor to a consumer product by adding fragrance and flavor compositions containing isomeric alkadienals or isomeric alkadienenitriles to the consumer product.

2. Description of the Related Art

Various alkenals and alkadienals having eight or more carbon atoms are known as fragrance materials or flavorings. For example, S. Arctander in "Perfume and Flavor Chemicals", names 2,4-decadienal and 2-decenal as fragrance materials but without any reference to cis or trans configuration, and 8-, 9- and 10-undecenal, of which 8- and 9-undecenal have the cis configuration. In U.S. Pat. Nos. 3,821,421 and 3,686,003, it is reported that both cis-4-decenal and cis, cis-4,7-tridecadienal and other polyunsaturated aldehydes containing 11-17 carbon atoms are suitable for imparting an aroma of chicken meat to foodstuffs.

In another publication, Meijboom et al (J. AM. Oil Chem. Soc. (1981), 58(6), 680-2) describes flavor perceptibility of straight chain, unsaturated aldehydes. These aldehydes include materials such as E,E-2,4-heptadienal (rancid hazelnuts), E,E-2,4-nonadienal (Nutty), E,E-2,5-octadienal (cucumber-like), E,E-2,6-nonadienal (tallowy, green), and E,E-2,7-decadienal (green, plant like). There is no reference to the corresponding E,Z isomers or use of these materials in fragrances.

Other dienals such as 2E,4E-decadienal, 2E,4E-undecadienal and 2E,6Z-dodecadienal have been reported and used in chicken meat flavor preparations. Further, Gerard Moschiano (Perfumer & Flavorist 23, No. 3, 55, 1998) describes the alkyl dienal, 2,4-decadienal as having fatty, chicken, fried, citrus, coriander and brothy odor. More recently, Delort et al. reported the identification and synthesis of several alkadienals found in extracts obtained from distinct parts of chicken (J. Agric. Food Chem. 2011, 59, 11752-11763).

In U.S. Pat. No. 3,928,402, a method of synthesis is described for γ-δ-unsaturated carbonyl compounds including aldehydes. Only compounds with a 2,4-diene system and/or an ester or keto group are disclosed.

In U.S. Pat. No. 3,920,752, it is reported that certain γ-δ-unsaturated aldehydes are valuable fragrance materials. From the structural formulae, only branched C-11 dienals with a trans-double bond at carbon 4 are disclosed. In U.S. Pat. No. 4,687,599, it is reported that cis,cis-4,7-decadienal, cis,cis-4,7,9-decatrienal and cis,cis-4,7,12-tridecatrienal are useful fragrance materials, but the trans-isomers are excluded.

There is an ongoing interest in the fragrance and flavor industry to use new compounds that enhance or improve organoleptic character and impart new notes to help perfumers and flavorists create exciting new fragrance and flavor experience desired by consumers. There remains a need and demand for unique fragrance and flavor compositions.

The present disclosure provides many advantages, which shall become apparent as described below.

SUMMARY OF THE DISCLOSURE

This disclosure relates in part to fragrance and flavor compositions containing isomeric alkadienals or isomeric alkadienenitriles. This disclosure also relates in part to a method of imparting a fragrance or flavor to a consumer product by adding fragrance and flavor compositions containing isomeric alkadienals or isomeric alkadienenitriles to the consumer product.

This disclosure also relates in part to a composition comprising at least one isomeric alkadienal or at least one isomeric alkadienenitrile in an amount effective to impart a fragrance or flavor to the composition.

This disclosure further relates in part to a fragrance or flavor composition comprising at least one isomeric alkadienal or at least one isomeric alkadienenitrile in an amount effective to impart a fragrance or flavor to the composition.

This disclosure yet further relates in part to a consumer product containing the fragrance or flavor composition comprising at least one isomeric alkadienal or at least one isomeric alkadienenitrile in an amount effective to impart a fragrance or flavor to the consumer product.

This disclosure also relates in part to a method of imparting a fragrance or flavor to a consumer product comprising adding to the consumer product a fragrance or flavor composition comprising at least one isomeric alkadienal or at least one isomeric alkadienenitrile in an amount effective to impart a fragrance or flavor to the consumer product.

Further objects, features and advantages of the present disclosure will be understood by reference to the following drawings and detailed description.

DESCRIPTION OF THE PREFERRED EMBODIMENTS

As used herein, the term "fragrance composition" refers to a mixture comprising one or more fragrance components, in any of their forms, and one or more solvents or perfuming co-ingredients. As known in the art, a fragrance composition will contain one or more fragrance components (e.g., perfuming co-ingredients) in order to impart an olfactory note to the composition (e.g., a household cleaner, perfume, or other commercial product) to which it is added. In one embodiment, the fragrance composition contains two or more fragrance components which, collectively and in combination with the solvent to which they are added, impart an intended olfactory note (e.g., a hedonically pleasing note) to a human in close proximity to the fragrance composition.

In general terms, perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin, and are known to perfumists of ordinary skill in the art. Many of these ingredients are listed in reference texts such as S. Arctander, Perfume and Flavor Chemicals, 1969, Montclair, N.J., USA or any of its more recent versions, each of which are hereby incorporated by reference.

As used herein, the term "perfume composition" refers a mixture of fragrance materials and optionally auxiliary substances, dissolved in a suitable solvent or mixed with a powdery substrate which is used to impart a desired odor to the skin and/or all types of products. Examples of such products include soaps, detergents, air fresheners, room sprays, pomanders, candles, cosmetics, such as creams, ointments, toilet waters, pre- and aftershave lotions, talcum powders, hair-care agents, body deodorants and anti-perspirants.

As used herein, the term "flavor composition" refers to a composition that contains one or more compound(s) (e.g., co-ingredients) that provide(s) a desired taste when combined with a solvent that is suitable for oral administration and oral consumption. Examples of flavoring co-ingredients that are generally included in a flavor composition are listed in S. Arctander, Perfume and Flavor Chemicals, 1969, Montclair, N.J., USA. The skilled person in the art of flavors is able to select them on the basis of its general knowledge and according to the nature of the product to be flavored and the desired taste.

As used herein, the term "flavor composition" refers to a mixture of flavor materials and optionally auxiliary substances, dissolved in a suitable solvent or mixed with a powdery substrate which is used to impart a desired taste to all types of products. Examples of such products include beverages, dairy products, confectionaries, cereals, snacks, soups and the like.

As used herein, the phrase "consumer product" refers to composition that is in a form ready for use by the consumer for the marketed indication. A solvent suitable for use in a consumer product is a solvent that, when combined with other components of the end product, will not render the consumer product unfit for its intended consumer use.

Any one of the isomeric alkadienal or isomeric alkadienenitrile compositions of this disclosure can be included in a fragrance or flavor composition. In one embodiment, any one of the isomeric alkadienal or isomeric alkadienenitrile compositions of this disclosure is provided in a fragrance composition. In an alternative embodiment, any one of the isomeric alkadienal or isomeric alkadienenitrile compositions of this disclosure is provided in a flavor composition.

As described herein, this disclosure relates to a composition comprising at least one isomeric alkadienal or at least one isomeric alkadienenitrile in an amount effective to impart a fragrance or flavor to the composition.

Also, as described herein, this disclosure relates to a fragrance or flavor composition comprising at least one isomeric alkadienal or at least one isomeric alkadienenitrile in an amount effective to impart a fragrance or flavor to the composition.

In the composition and the fragrance or flavor composition, the at least one isomeric alkadienal or the at least one isomeric alkadienenitrile has from about 0.1 percent to about 99.5 percent of E,Z isomers, from about 0.1 percent to about 99.5 percent of Z,E isomers, from about 0.1 percent to about 99.5 percent of E,E isomers, and from about 0.1 percent to about 99.5 of Z,Z isomers, based on the total Z and E isomers in the composition or in the fragrance or flavor composition.

In an embodiment, in the composition and the fragrance or flavor composition, the at least one isomeric alkadienal or the at least one isomeric alkadienenitrile has from about 10 percent to about 98 percent of E,Z isomers, preferably from about 15 percent to about 98 percent of E,Z isomers, and more preferably from about 20 percent to about 98 percent of E,Z isomers; from about 0.5 percent to about 40 percent of Z,E isomers, preferably from about 0.5 percent to about 38 percent of Z,E isomers, and more preferably from about 0.5 percent to about 35 percent of Z,E isomers; from about 0.1 percent to about 40 percent of E,E isomers, preferably from about 0.1 percent to about 38 percent of E,E isomers, and more preferably from about 0.1 percent to about 35 percent of E,E isomers; and from about 2 percent to about 40 percent of Z,Z isomers, preferably from about 2 percent to about 38 percent of Z,Z isomers, and more preferably from about 2 percent to about 35 percent of Z,Z isomers; based on the total Z and E isomers in the composition or in the fragrance or flavor composition.

Further, in an embodiment, the at least one isomeric alkadienal or the at least one isomeric alkadienenitrile has from about 10 percent to about 98 percent of E,Z isomers, preferably from about 20 percent to about 90 percent of E,Z isomers, and more preferably from about 30 percent to about 80 percent of E,Z isomers, based on the total Z and E isomers in the composition.

In an embodiment, this disclosure relates in part to isomeric alkadienals and isomeric alkadienenitriles and their use in fragrance and flavor compositions. In particular, this disclosure provides isomeric 2,6-, 2,7-, 2,8-, 2,9-, 2,10-, 2,11-, 2,12-, 2,13- and 2,14-alkadienals and isomeric 2,6-, 2,7-, 2,8-, 2,9-, 2,10-, 2,11-, 2,12-, 2,13- and 2,14-alkadienenitriles and their use in fragrance and flavor compositions. More, in particular, this disclosure provides the use of 2-trans and 6-, 7-, 8-, 9-, 10-, 11-, 12-, 13- and 14-cis alkadienal isomers and 2-trans and 6-, 7-, 8-, 9-, 10-, 11-, 12-, 13- and 14-cis alkadienenitrile isomers for use in perfumery and flavor applications.

In another embodiment, this disclosure relates in part to a fragrance or flavor composition comprising an effective amount of at least one isomeric alkadienal or at least one isomeric alkadienenitrile. The at least one isomeric alkadienal includes, for example, E,Z-2,6-octadienal, E,Z-2,7-nonadienal, E,Z-2,6-decadienal, E,Z-2,7-decadienal, E,Z-2,7-undecadienal, E,Z-2,8-undecadienal, E,Z-2,10-tridecadienal, E,Z-2,7-tetradecadienal, E,Z-2,11-tetradecadienal, 5-methyl-E,Z-2,7-nonadienal, or 5-methyl-E,Z-2,7-decadienal. The at least one isomeric alkadienenitrile includes, for example, E,Z-2,6-octadienenitrile, E,Z-2,7-nonadienenitrile, E,Z-2,7-decadienenitrile, E,Z-2,8-decadienenitrile, E,Z-2,8-undecadienenitrile, E,Z-2,9-dodecadienenitrile, E,Z-2,10-tridecadienenitrile, or E,Z-2,11-tetradecadienenitrile. The composition may also have smaller amounts of other isomers related to each alkadienal or alkadienenitrile as described herein.

Illustrative isomeric alkadienals of this disclosure include, for example, isomers of 2,6-alkadienal, 2,7-alkadienal, 2,8-alkadienal, 2,9-alkadienal, 2,10-alkadienal, 2,11-alkadienal, 2,12-alkadienal, 2,13-alkadienal, 2,14-alkadienal, and the like.

More particularly, illustrative isomers of 2,6-alkadienal include, for example, the isomers of 2,6-heptadienal, 2,6-octadienal, 2,6-nonadienal, 2,6-decadienal, 2,6-undecadienal, 2,6-dodecadienal, 2,6-tridecadienal, 2,6-tetradecadienal, 2,6-pentadecadienal, and the like. Illustrative isomers of 2,7-alkadienal include, for example, the isomers of 2,7-octadienal, 2,7-nonadienal, 2,7-decadienal, 2,7-undecadienal, 2,7-dodecadienal, 2,7-tridecadienal, 2,7-tetradecadienal, 2,7-pentadecadienal, and the like. Illustrative isomers of 2,8-alkadienal include, for example, the isomers of 2,8-nonadienal, 2,8-decadienal, 2,8-undecadienal, 2,8-dodecadienal, 2,8-tridecadienal, 2,8-tetradecadienal, 2,8-pentadecadienal, and the like. Illustrative isomers of 2,9-alkadienal include, for example, the isomers of 2,9-decadienal, 2,9-undecadienal, 2,9-dodecadienal, 2,9-tridecadienal, 2,9-tetradecadienal, 2,9-pentadecadienal, and the like. Illustrative isomers of 2,10-alkadienal include, for example, the isomers of 2,10-undecadienal, 2,10-dodecadienal, 2,10-tridecadienal, 2,10-tetradecadienal, 2,10-pentadecadienal, and the like. Illustrative isomers of 2,11-alkadienal include, for example, the isomers of 2,11-dodecadienal, 2,11-tridecadienal, 2,11-tetradecadienal, 2,11-pentadecadienal, and the like. Illustrative isomers of 2,12-alkadienal include, for example, the isomers of 2,12-tridecadienal, 2,12-tetradecadienal, 2,12-pentadecadienal, and the like. Illustrative isomers of 2,13-alkadienal include, for example, the isomers of 2,13-tetradecadienal, 2,13-pentadecadienal, and the like. Illustrative isomers of 2,14-alkadienal include, for example, the isomers of 2,14-pentadecadienal, and the like.

Preferred isomeric alkadienals of this disclosure include, for example, E,Z-2,6-octadienal, E,Z-2,7-nonadienal, E,Z-2,6-decadienal, E,Z-2,7-decadienal, E,Z-2,7-undecadienal, E,Z-2,8-undecadienal, E,Z-2,10-tridecadienal, E,Z-2,7-tetradecadienal, E,Z-2,11-tetradecadienal, 5-methyl-E,Z-2,7-nonadienal, and 5-methyl-E,Z-2,7-decadienal.

Preferred isomeric alkadienals of this disclosure can be represented by the formula

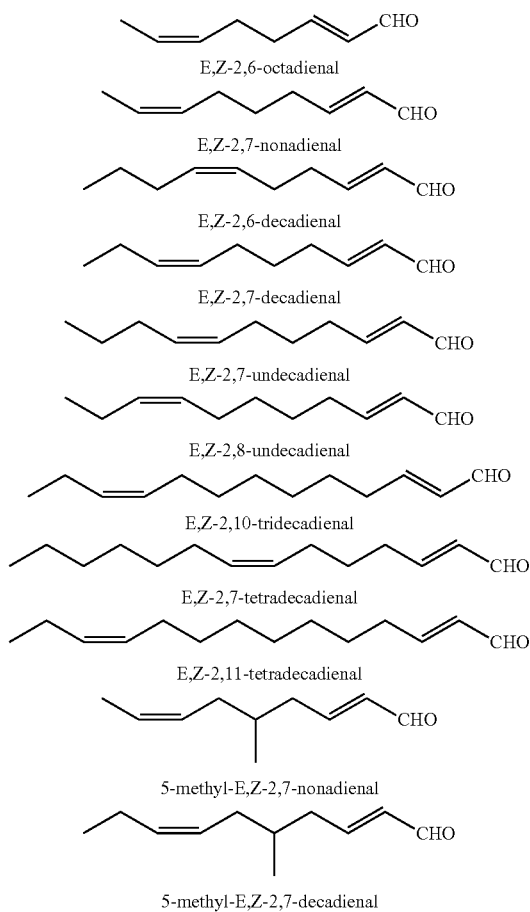

Illustrative isomeric alkadienenitriles of this disclosure include, for example, isomers of 2,6-alkadienenitrile, 2,7-alkadienenitrile, 2,8-alkadienenitrile, 2,9-alkadienenitrile, 2,10-alkadienenitrile, 2,11-alkadienenitrile, 2,12-alkadienenitrile, 2,13-alkadienenitrile, 2,14-alkadienenitrile, and the like.

More particularly, illustrative isomers of 2,6-alkadienenitrile include, for example, the isomers of 2,6-heptadienenitrile, 2,6-octadienenitrile, 2,6-nonadienenitrile, 2,6-decadienenitrile, 2,6-undecadienenitrile, 2,6-dodecadienenitrile, 2,6-tridecadienenitrile, 2,6-tetradecadienenitrile, 2,6-pentadecadienenitrile, and the like. Illustrative isomers of 2,7-alkadienenitrile include, for example, the isomers of 2,7-octadienenitrile, 2,7-nonadienenitrile, 2,7-decadienenitrile, 2,7-undecadienenitrile, 2,7-dodecadienenitrile, 2,7-tridecadienenitrile, 2,7-tetradecadienenitrile, 2,7-pentadecadienenitrile, and the like. Illustrative isomers of 2,8-alkadienenitrile include, for example, the isomers of 2,8-nonadienenitrile, 2,8-decadienenitrile, 2,8-undecadienenitrile, 2,8-dodecadienenitrile, 2,8-tridecadienenitrile, 2,8-tetradecadienenitrile, 2,8-pentadecadienenitrile, and the like. Illustrative isomers of 2,9-alkadienenitrile include, for example, the isomers of 2,9-decadienenitrile, 2,9-undecadienenitrile, 2,9-dodecadienenitrile, 2,9-tridecadienenitrile, 2,9-tetradecadienenitrile, 2,9-pentadecadienenitrile, 2,9-pentadecadienenitrile, and the like. Illustrative isomers of 2,10-alkadienenitrile include, for example, the isomers of 2,10-undecadienenitrile, 2,10-dodecadienenitrile, 2,10-tridecadienenitrile, 2,10-tetradecadienenitrile, 2,10-pentadecadienenitrile, and the like. Illustrative isomers of 2,11-alkadienenitrile include, for example, the isomers of 2,11-dodecadienenitrile, 2,11-tridecadienenitrile, 2,11-tetradecadienenitrile, 2,11-pentadecadienenitrile, and the like. Illustrative isomers of 2,12-alkadienenitrile include, for example, the isomers of 2,12-tridecadienenitrile, 2,12-tetradecadienenitrile, 2,12-pentadecadienenitrile, and the like. Illustrative isomers of 2,13-alkadienenitrile include, for example, the isomers of 2,13-tetradecadienenitrile, 2,13-pentadecadienenitrile, and the like. Illustrative isomers of 2,14-alkadienenitrile include, for example, the isomers of 2,14-pentadecadienenitrile, and the like.

Preferred isomeric alkadienenitriles of this disclosure include, for example, E,Z-2,6-octadienenitrile, E,Z-2,7-nonadienenitrile, E,Z-2,7-decadienenitrile, E,Z-2,8-decadienenitrile, E,Z-2,8-undecadienenitrile, E,Z-2,9-dodecadienenitrile, E,Z-2,10-tridecadienenitrile, and E,Z-2,11-tetradecadienenitrile.

Preferred isomeric alkadienenitriles of this disclosure can be represented by the formula

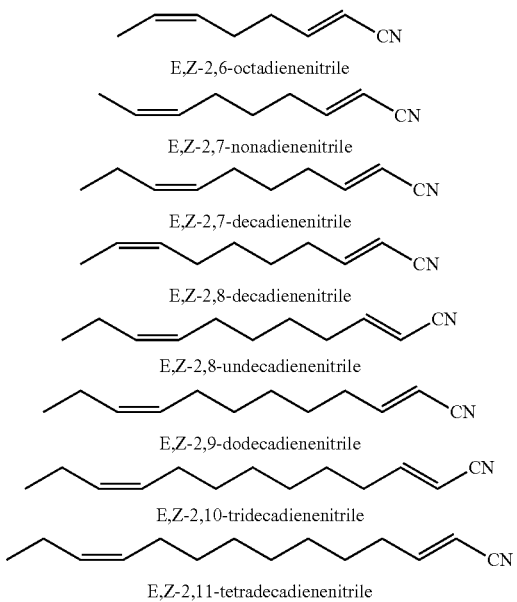

For the fragrance compositions of this disclosure, the at least one isomeric alkadienal or the at least one isomeric alkadienenitrile is present in an amount of at least about 1 ppm by weight, based on the total weight of the composition, to impart a fragrance to the composition.

For the flavor compositions of this disclosure, the at least one isomeric alkadienal or the at least one isomeric alkadienenitrile is present in an amount of at least about 0.1 ppm by weight, based on the total weight of the composition, to impart a flavor to the composition.

For the fragrance compositions of this disclosure, the at least one isomeric alkadienal or the at least one isomeric alkadienenitrile can be combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-01, phenoxyethylisobutyrate, phenylacetaldehydedimethylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

For the flavor compositions of this disclosure, the at least one isomeric alkadienal or the at least one isomeric alkadienenitrile can be combined with geraniol, geranyl acetate, linalool, linalyl acetate, citronellol, citronellyl acetate, terpineol, terpinyl acetate, 2-phenylethanol, 2-phenylethyl acetate, benzyl alcohol, benzyl acetate, benzyl salicylate, heliotropine, benzaldehyde, anisaldehyde, benzyl salicylate, e, n-decanal, n-dodecanal, 9-decen-1-ol, coumarin, eugenol, vanillin, hexanal, eucalyptol, ionones, methylionones, isomethylionones, irones, cis-3-hexenol and esters of the latter, acetaldehyde, ethyl acetate, ethyl butyratecinnamic aldehyde, cuminic aldehyde, furfural, cinnamic aldehyde, maltol, ethyl maltol, dimethyl sulfide, gamma decalactone, gamma undecalactone, diacetyl, ethyl valerate, damascone, damascenone, methyl caproate, cyclotene, butyric acid, acetoin, delta decalactone, furaneol, acetoin, benzodihydro pyrone, 2,6-nonadienal, melonal or methyl heptane carbonate, to impart a flavor to the composition.

In an embodiment, this disclosure also relates in part to the preparation of alkadienals and alkadienenitriles for use in fragrance and flavor formulations. These alkadienals and alkadienenitriles have a range of unexpected and unobvious organoleptic properties described as fresh, strong, fruity, floral, and highly diffusive. These notes are highly desirable in creating consumer acceptable fragrances and flavors. Additionally, these alkadienals and alkadienenitriles are extremely cost effective since they possess high odor intensity and can be effective at imparting the desirable organoleptic effect to a fragrance or flavor at a very low concentration.

In accordance with this disclosure, the isomeric alkadienals and the isomeric alkadienenitriles of this disclosure can be prepared by conventional processes. The compositions of this disclosure and the fragrance and flavor compositions of this disclosure can also be prepared by conventional processes.

The isomeric alkadienals of this disclosure have a range of fresh, watery, ozone, iris, aldehydic notes of exceptional strength. They also have fresh citrus, fruity, spicy taste suited to enhance a range of flavors for the food products.

As described herein, this disclosure provides a consumer product containing the fragrance or flavor composition comprising at least one isomeric alkadienal or at least one isomeric alkadienenitrile in an amount effective to impart a fragrance or flavor to the consumer product.

As further described herein, this disclosure provides a method of imparting a fragrance or flavor to a consumer product comprising adding to the consumer product a fragrance or flavor composition comprising at least one isomeric alkadienal or at least one isomeric alkadienenitrile in an amount effective to impart a fragrance or flavor to the consumer product.

Illustrative consumer fragrance products useful in this disclosure include, for example, a candle, an air care product, a perfume, a cologne, a soap, a personal care product, a detergent, a fabric care product, a household cleaning product, and the like.

More particularly, illustrative consumer fragrance products include a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

Preferred illustrative consumer fragrance products include an air care product, a perfume, and a cologne.

Illustrative consumer flavor products useful in this disclosure include, for example, a beverage, a powder or semi-frozen/frozen concentrate for a drink, a candy, a sugarless candy, a chocolate, a chewing gum, a bubble gum, a condiment, a spice, a seasoning, a dry cereal, an oatmeal, a granola bar, an alcoholic beverage, an energy beverage, a juice, a tea, a coffee, a salsa, a gel bead, a film strip for halitosis, a lozenge, a cough drop, a throat lozenge, a throat spray, a toothpaste, and a mouth rinse.

More particularly, illustrative consumer flavor products include a beverage, a dairy product, a confectionary, a cereal, a snack, and a soup.

Preferred illustrative consumer flavor products include a beverage, a chewing gum, and a bubble gum.

In an embodiment, one or more of the isomeric alkadienals or isomeric alkadienenitriles of the present disclosure, alone or in combination with other co-ingredients, can be employed in fragrance and flavor compositions, solvents, media and the like. As indicated herein, the use of such isomeric alkadienals or isomeric alkadienenitriles is applicable to a wide variety of products in the fragrance industry such as, but not limited to: candles; air fresheners; perfumes; colognes; personal care products such as soaps, deodorants, shampoos, conditioners, shower gels and shaving lotions; cosmetics such as lotions and ointments; as well as detergents; fabric care products and household cleaner/cleaning agents. Also, as indicated herein, the use of such isomeric alkadienals or isomeric alkadienenitriles is also applicable to a wide variety of products in the flavor industry such as, but not limited to: foodstuffs such as baked goods, dairy products, desserts, etc.; beverages such as juices, sodas, teas, flavored waters, fruit-based "smoothie" drinks, milk-based drinks, etc.; confectionaries such as sweets, hard candy, gums; and gelatinous materials, snacks, desserts, pharmaceuticals, oral care products and the like.

As the isomeric alkadienals or isomeric alkadienenitriles of the present disclosure are useful ingredients for the perfuming or flavoring of various products, the present disclosure also concerns all different forms of the isomeric alkadienals or isomeric alkadienenitriles that can be advantageously employed in perfumery or in flavors. Such forms include a composition including isomeric alkadienals or isomeric alkadienenitriles and a solvent commonly used in perfumery or in flavor compositions. Examples of such solvents used in perfumery are known in the art and include, but are not limited to: dipropyleneglycol, diethyl phthalate, isopropyl myristate, benzyl benzoate, 2-(2-ethoxy)-1-ethanol, ethyl citrate, ethanol, water/ethanol mixtures, limonene or other terpenes, isoparaffins such as those known under the trademark Isopar™ (ExxonMobil Chemicals, Houston, Tex.), and glycol ethers and glycol ether esters such as those known under the trademark Dowanol™ (Dow Chemical Company, Midland Mich.). Examples of solvents commonly used in flavors are also known in the art and include, but are not limited to: propylene glycol, triacetin, triethyl citrate, benzyl alcohol, benzyl benzoate, ethanol, vegetable oils and terpenes.

The isomeric alkadienals or isomeric alkadienenitriles of the present disclosure are particularly valuable as being capable of imparting green, fruity, floral, or woody notes to a fragrance composition. For example, E,Z-2,7-decadienenitrile can be used to impart a green, fruity, floral, woody characteristic to fragrance compositions. For fragrance applications, typical concentrations of the isomeric alkadienals or isomeric alkadienenitriles are on the order of 0.01 ppm to 1% by weight, or more, based on the total weight of the composition into which the fragrance compound is incorporated. Those skilled in the art will be able to employ the desired level of the compounds of the disclosure to provide the desired fragrance/flavor and intensity. In general, the isomeric alkadienals or isomeric alkadienenitriles of the present disclosure will be used in relatively small amounts, typically via significant dilutions due to their high-impact, diffusive properties.

The perfuming compositions according to the disclosure may be in the form of a simple mixture of the various co-ingredients and solvents, or also in the form of a biphasic system such as an emulsion or microemulsion. Such systems are well-known to persons skilled in the art.

As described herein, suitable perfumed end products that can include a composition of the present disclosure including, but are not limited to: 1) candles, air fresheners, perfumes and colognes, 2) personal care products such as soaps, deodorants, shampoos, conditioners, shower gels and shaving lotions; 3) cosmetics such as lotions and ointments; as well as 4) detergents, fabric care products and household cleansers/cleaning agents. Depending on the solvents that may be present in some end products, it may be necessary to protect the isomeric alkadienals or isomeric alkadienenitriles from premature degradation, for example by encapsulation or with a stabilizer, or other methods well-known to those of ordinary skill in the art.

The compositions of the present disclosure can also be added to, for example: 1) fragrance products; perfume; eau de perfume; eau de toilet; eau de cologne; and the like; skin-care cosmetics, face washing creams, varnishing creams, cleansing creams, cold creams, massage creams and oils, milky lotions, skin toning lotion, cosmetic solutions, packs, makeup remover, and the like; 2) makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; 3) hair care cosmetics, pomades, brilliantines, setting lotions, hair sticks, hair solids, hair oils, hair treatments, hair creams, hair tonics, hair liquids, hair sprays, hair restorers, hair dyes, and the like; 4) sunburn cosmetics, suntan products, sunscreen products, and the like; 5) medical cosmetics, antiperspirants, after-shave lotions and gels, permanent wave lotions, medicated soaps, medicated shampoos, medicated skin care products, and the like; 6) hair care products, shampoos, rinses, shampoo-including-rinses, hair conditioners, hair treatments, hair packs, and the like; 7) as soaps, toilet soaps, bath soaps, perfumed soaps, transparent soaps, synthetic soaps, and the like; 8) body washing soaps, body soaps, body shampoos, hand soaps, and the like; 9) bathing, bathing agents (e.g., bath salts, bath tablets, bath liquids, and the like), foam baths (bubble bath and the like), bath oils (e.g., bath perfumes, bath capsules and the like), milk baths, bath gels, bath cubes, and the like; 10) detergents, heavy duty detergents for clothes, light duty detergents for clothes, liquid detergents, laundering soaps, compact detergents, powder soaps, and the like; 11) softening finishing agents, softeners, furniture care products, and the like; and deodorants, aromatic substances and the like; 12) insect repellent, insecticides, and the like; 13) oral care products such as tooth pastes, mouth cleaners, mouth wash, troches, chewing gums, and the like; and 14) pharmaceutical products, poultices, external skin care pharmaceuticals such as ointments, internal administration medicines, and the like.

Furthermore, the compositions of the disclosure, in any of their forms, can also be incorporated into flavoring compositions or flavored products, together with co-ingredients or adjuvants, e.g., to impart taste to flavoring compositions, foods or beverages. Consequently, the use of the compositions of the present disclosure, in any of their forms, as flavoring ingredients, is another object of the present disclosure, as is a flavor composition comprising an isomeric alkadienal or isomeric alkadienenitrile of the present disclosure.

The flavor compositions according to the disclosure may be in the form of a simple mixture of flavoring ingredients or in an encapsulated form, e.g., a flavoring composition entrapped into a solid matrix that may comprise wall-forming and plasticizing materials such as mono-, di- or trisaccharides, natural or modified starches, hydrocolloids, cellulose derivatives, polyvinyl acetates, polyvinylalcohols, proteins or pectins. Examples of particularly useful matrix materials include, for example, sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylinethyl cellulose, derivatives, gelatin, agar, alginate and mixtures thereof. Encapsulation is well-known to persons skilled in the art, and may be performed, for instance, using techniques such as spray-drying, agglomeration or extrusion, or coating encapsulation, including coacervation and complex coacervation techniques.

The compositions of the present disclosure are particularly valuable as being capable of imparting tropical, berry, bakery, caramel, watermelon, and vegetable notes, to flavor ingredients. Specifically, E,Z-2,7-undecadienals and E,Z-2,8-undecadienals can be used to impart a watermelon characteristic to flavor compositions. For flavor applications, typical concentrations of isomeric alkadienals or isomeric alkadienenitriles are on the order of 0.1 ppb-100 ppm. Preferably, applicable concentrations fall in the range of 0.001 ppm-0.01 ppm. Those skilled in the art will be able to employ the desired level of the isomeric alkadienals or isomeric alkadienenitriles to provide the desired flavor and intensity. Much higher concentrations may be employed when the compounds are used in concentrated flavors and flavor compositions.

In an embodiment, a composition of the present disclosure is used in chewing and bubble gums and confectionaries (e.g., hard or soft candies or lozenges). Chewing gum compositions typically include one or more gum bases and other standard components such as flavoring agents, softeners, sweeteners and the like. Flavoring agents for use in chewing gum compositions are well known and include natural flavors such as citrus oils, peppermint oil, spearmint oil, oil of wintergreen, natural menthol, cinnamon, ginger and the like; artificial flavors such as menthol, carvone, limonene, cinnamic aldehyde, linalool, geraniol, ethyl butyrate, and the like. As is known in the art, the ingredients used in chewing gum compositions can include sweeteners, both natural and artificial and both sugar and sugarless. Sweeteners are typically present in the chewing gum compositions in amounts of from about 20% to 80% by weight, preferably from about 30% to 60% by weight, based on the total weight of the chewing gum composition. Sugarless sweeteners include, but are not limited sugar alcohols such as Sorbitol, manifold, xylitol, hydrogenated starch hydrolysates, malitol and the like. High intensity sweeteners such as sucralose, aspartame, neotame, salts of acesulfame, and the like, when employed, are typically present up to about 1.0% by weight.

In an alternative embodiment, a composition of the present disclosure is included in an oral personal care product (e.g., a mouthwash or toothpaste). For example, a mouthwash can be prepared by dissolving a flavor composition (e.g., a flavor cocktail) (liquid or powder) that includes a composition of the present disclosure in a solvent (e.g., water) that further includes, for example, a flavor such as menthol and a surfactant; and then mixing the resulting solution with, for example, an aqueous erythritol solution.

In one embodiment of the present disclosure, a composition of the present disclosure is added, directly or indirectly, to a pharmaceutical dosage form (e.g., a tablet, capsule, drop or lozenge) that contains a therapeutically active agent (e.g., a medicament). For example, one embodiment of the present disclosure provides a cough drop or lozenge containing one or more compositions of the present disclosure and, optionally, further containing menthol or other medicaments for the treatment of sore throat, coughing or other upper respiratory ailments.

One or more of the present compositions can also be added to, for example, compositions for the preparation of: 1) carbonated or non-carbonated fruit beverages, carbonated cola drinks, wine coolers, fruit liquors, cordials, milk drinks, smoothie drinks, flavored water, tropical alcoholic and "virgin" drink mixes (e.g. margarita, pina colada or "rum-runner" concentrates), and powders for drinks (e.g., powdered sports or "hydrating" drinks); 2) frozen confectioneries such as ice creams, sherbets, and ice-lollies, hard candies, soft candies, taffies, chocolates, and sugarless candies; 3) desserts such as jelly and pudding; 4) confectioneries such as cakes, cookies, chewing gums and bubble gums; 5) condiments, spices and seasonings, dry cereals, oatmeals, and granola bars; 6) alcoholic beverages, energy beverages, juices, teas, coffees, salsa, and gel beads; 7) film strips for halitosis, and oral personal care products; 8) gelatin candies, pectin candies, starch candies, lozenges, cough drops, throat lozenges, throat sprays, and toothpastes.

The present compositions may also be added to, for example; 1) confectioneries such as buns with jam filling, and bars of sweet jellied paste; 2) jams; candies; 3) breads; 4) beverages such as green tea, oolong tea, black tea, persimmon leaf tea, Chamomile tea, Sasa veitchii tea, mulberry leaf tea, Houttuynia cordata tea, Puer tea, Mate tea, Rooibos tea, Gimunema tea, Guava tea, coffee, espresso, and hot and cold espresso and coffee products obtained by mixing espresso and/or coffee with milk, water or other liquids suitable for oral consumption (e.g., lattes, cafe au lait, cafe mocha) and cocoa; 5) soups such as Japanese flavor soup, western flavor soup, and Chinese flavor soup; 6) seasonings; 7) various instant beverages and foods; 8) various snack foods; and 9) other compositions for oral use.

As described herein, the compositions of this disclosure can be used in a broad range of fragrance and flavor applications, e.g., fine fragrances, household products, laundry products, personal care products and cosmetics. The flavor use can be in foodstuffs such as soups, beverages, dairy products, confectionaries, cereals, snack, etc. These compositions can be employed in widely varying amounts, depending upon the specific application and on the nature and amounts of other odor or taste carrying ingredients. But because of the exceptional strength of these compositions, the effect can be achieved at a very low level of incorporation.

Fragrances in consumer products provide several functions. They mask base odors, provide aesthetic pleasure and signal product attributes and function to the user, e.g., hygiene, cleanliness, mildness. Notwithstanding these benefits, it is also true that perfumes can cause a myriad of problems within products they have been added to, e.g., discoloration, phase separation, problems such as irritation and occasional allergic reaction to the user. Additionally, fragrances represent one of the more expensive components of the product and many fragrance ingredients may not be easily biodegradable. Over the years, perfume levels in many consumer products have increased by the popular demand but at the same time consumers have also become more critical of the fragranced products they purchase and use.

Therefore, in an embodiment, this disclosure provides high intensity consumer acceptable fragrances and desirable hedonics at a much lower concentration than achieved before. This lowering of fragrance concentration in consumer products by an order of magnitude has the benefit of cost saving, less interference with the physical properties of the product base, minimizing toxicological implications on the user, and lowering the environmental impact of chemicals used.

Fragrance materials and mixtures of fragrance materials which can be used in combination with the compositions of this disclosure for manufacturing perfume compositions include, for example, natural products, such as essential oils, absolutes, resinoids, resins, concretes, etc., but also synthetic fragrance materials such as hydrocarbons, alcohols, aldehydes, ketones, ethers, acids, esters, acetals, ketals, nitriles, etc., including saturated and unsaturated compounds, aliphatic carbocyclic and heterocyclic compounds.

Examples of fragrance materials which can be used in combination with the compositions of the disclosure include, for example, geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-01, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetralinemusks, isochromane-musks, macrocyclic ketones, macrolactone-musks, ethylene brassylate, aromatic nitromusks, and the like.

Auxiliary substances and solvents which can be used in perfume compositions of this disclosure include, for example, ethanol, isopropanol, dipropylene glycol, dipropyleneglycol monomethyl ether, diethylphthalate, and the like.

The quantities in which the compositions of this disclosure can be used in perfume compositions or in products to be perfumed can vary within wide limits and depend inter alia on the nature of the product in which the fragrance material is used, on the nature and quantity of the other components in the perfume composition and on the odor effect which is aimed at. It is therefore only possible to specify very rough limits, which, however, provide sufficient information for the specialist to be able to use the compounds according to the disclosure independently. In most cases a quantity of only 1 ppm in a perfume composition will already be sufficient to obtain a clearly perceptible odor effect. On the other hand, to achieve special odoriferous effects it is possible to use quantities of 100, 1000, 5000 ppm or even more in a composition. In products perfumed with such compositions, these concentrations are proportionately lower, depending on the quantity of composition used in the product.

There are three basic stages of a fragrance. The first stage (i.e., top notes) is the first impression that a fragrance gives to a customer. This initial stage is the most volatile. In the second stage (i.e., middle notes), a few moments after the application of a fragrance, the heart is revealed. This modifying part of the fragrance has medium volatility. In the third stage (i.e., base notes), after a fragrance dries down, these notes are more pronounced. This part of the fragrance is the longest lasting. The balance between these three groups is very important. In a well-balanced fragrance, it is important to understand what group or groups are the most important for a particular application. The fragrance compositions of this disclosure exemplify a desirable balance between these three groups for desired applications.

Flavor materials and mixtures of flavor materials which can be used in combination with the compositions of this disclosure for manufacturing flavor compositions are, for example, natural products, such as essential oils, absolutes, resinoids, resins, concretes, etc., but also synthetic flavor materials such as hydrocarbons, alcohols, aldehydes, ketones, ethers, acids, esters, acetals, ketals, etc., including saturated and unsaturated compounds, aliphatic carbocyclic and heterocyclic compounds.

Examples of flavor materials which can be used in combination with the compositions of the disclosure include, for example, geraniol, geranyl acetate, linalool, linalyl acetate, citronellol, citronellyl acetate, terpineol, terpinyl acetate, 2-phenylethanol, 2-phenylethyl acetate, benzyl alcohol, benzyl acetate, benzyl salicylate, heliotropine, benzaldehyde, anisaldehyde, benzyl salicylate, e, n-decanal, n-dodecanal, 9-decen-1-01, coumarin, eugenol, vanillin, hexanal, eucalyptol, ionones, methylionones, isomethylionones, irones, cis-3-hexenol and esters of the latter, acetaldehyde, ethyl acetate, ethyl butyratecinnamic aldehyde, cuminic aldehyde, furfural, cinnamic aldehyde, maltol, ethyl maltol, dimethyl sulfide, gamma decalactone, gamma undecalactone, diacetyl, ethyl valerate, damascone, damascenone, methyl caproate, cyclotene, butyric acid, acetoin, delta decalactone, furaneol, acetoin, benzodihydro pyrone, 2,6-nonadienal, melonal, methyl heptane carbonate, and the like.

Auxiliary substances and solvents which can be used in flavor compositions of this disclosure include, for example, ethanol, propylene glycol, and the like.

Preferred embodiments of this disclosure are described in the clauses below.

1. A composition comprising at least one isomeric alkadienal or at least one isomeric alkadienenitrile in an amount effective to impart a fragrance or flavor to the composition.

2. A fragrance or flavor composition comprising at least one isomeric alkadienal or at least one isomeric alkadienenitrile in an amount effective to impart a fragrance or flavor to the composition.

3. A method of imparting a fragrance or flavor to a consumer product comprising adding to the consumer product a fragrance or flavor composition comprising at least one isomeric alkadienal or at least one isomeric alkadienenitrile in an amount effective to impart a fragrance or flavor to the consumer product.

4. The composition of clause 1, the fragrance or flavor composition of clauses 2, and the method of clause 3, wherein the at least one isomeric alkadienal or the at least one isomeric alkadienenitrile has from about 0.1 percent to about 99.5 percent of E,Z isomers, from about 0.1 percent to about 99.5 percent of Z,E isomers, from about 0.1 percent to about 99.5 percent of E,E isomers, and from about 0.1 percent to about 99.5 of Z,Z isomers, based on the total Z and E isomers in the composition.

5. The composition of clause 1, the fragrance or flavor composition of clause 2, and the method of clause 3, wherein the at least one isomeric alkadienal or the at least one isomeric alkadienenitrile has from about 10 percent to about 98 percent of E,Z isomers, from about 0.5 percent to about 40 percent of Z,E isomers, from about 0.1 percent to about 40 percent of E,E isomers, and from about 2 percent to about 40 percent of Z,Z isomers, based on the total Z and E isomers in the composition.

6. The composition of clause 1, the fragrance or flavor composition of clause 2, and the method of clause 3, wherein the at least one isomeric alkadienal is selected from the group consisting of isomers of 2,6-alkadienal, 2,7-alkadienal, 2,8-alkadienal, 2,9-alkadienal, 2,10-alkadienal, 2,11-alkadienal, 2,12-alkadienal, 2,13-alkadienal, and 2,14-alkadienal.

7. The composition of clause 1, the fragrance or flavor composition of clause 2, and the method of clause 3, wherein the at least one isomeric alkadienenitrile is selected from the group consisting of isomers of 2,6-alkadienenitrile, 2,7-alkadienenitrile, 2,8-alkadienenitrile, 2,9-alkadienenitrile, 2,10-alkadienenitrile, 2,11-alkadienenitrile, 2,12-alkadienenitrile, 2,13-alkadienenitrile, and 2,14-alkadienenitrile.

8. The composition of clause 1, the fragrance or flavor composition of clause 2, and the method of clause 3, wherein the isomers of 2,6-alkadienal are selected from the group consisting of isomers of 2,6-heptadienal, 2,6-octadienal, 2,6-nonadienal, 2,6-decadienal, 2,6-undecadienal, 2,6-dodecadienal, 2,6-tridecadienal, 2,6-tetradecadienal, and 2,6-pentadecadienal; the isomers of 2,7-alkadienal are selected from the group consisting of isomers of 2,7-octadienal, 2,7-nonadienal, 2,7-decadienal, 2,7-undecadienal, 2,7-dodecadienal, 2,7-tridecadienal, 2,7-tetradecadienal, and 2,7-pentadecadienal; the isomers of 2,8-alkadienal are selected from the group consisting of isomers of 2,8-nonadienal, 2,8-decadienal, 2,8-undecadienal, 2,8-dodecadienal, 2,8-tridecadienal, 2,8-tetradecadienal, and 2,8-pentadecadienal; the isomers of 2,9-alkadienal are selected from the group consisting of isomers of 2,9-decadienal, 2,9-undecadienal, 2,9-dodecadienal, 2,9-tridecadienal, 2,9-tetradecadienal, and 2,9-pentadecadienal; the isomers of 2,10-alkadienal are selected from the group consisting of isomers of 2,10-undecadienal, 2,10-dodecadienal, 2,10-tridecadienal, 2,10-tetradecadienal, and 2,10-pentadecadienal; the isomers of 2,11-alkadienal are selected from the group consisting of isomers of 2,11-dodecadienal, 2,11-tridecadienal, 2,11-tetradecadienal, and 2,11-pentadecadienal; the isomers of 2,12-alkadienal are selected from the group consisting of isomers of 2,12-tridecadienal, 2,12-tetradecadienal, and 2,12-pentadecadienal; the isomers of 2,13-alkadienal are selected from the group consisting of the isomers of 2,13-tetradecadienal and 2,13-pentadecadienal; and the isomers of 2,14-alkadienal are selected from isomers of 2,14-pentadecadienal.

9. The composition of clause 1, the fragrance or flavor composition of clause 2, and the method of clause 3, wherein the isomers of 2,6-alkadienenitrile are selected from the group consisting of isomers of 2,6-heptadienenitrile, 2,6-octadienenitrile, 2,6-nonadienenitrile, 2,6-decadienenitrile, 2,6-undecadienenitrile, 2,6-dodecadienenitrile, 2,6-tridecadienenitrile, 2,6-tetradecadienenitrile, and 2,6-pentadecadienenitrile; the isomers of 2,7-alkadienenitrile are selected from the group consisting of isomers of 2,7-octadienenitrile, 2,7-nonadienenitrile, 2,7-decadienenitrile, 2,7-undecadienenitrile, 2,7-dodecadienenitrile, 2,7-tridecadienenitrile, 2,7-tetradecadienenitrile, and 2,7-pentadecadienenitrile; the isomers of 2,8-alkadienenitrile are selected from the group consisting of isomers of 2,8-nonadienenitrile, 2,8-decadienenitrile, 2,8-undecadienenitrile, 2,8-dodecadienenitrile, 2,8-tridecadienenitrile, 2,8-tetradecadienenitrile, and 2,8-pentadecadienenitrile; the isomers of 2,9-alkadienenitrile are selected from the group consisting of isomers of 2,9-decadienenitrile, 2,9-undecadienenitrile, 2,9-dodecadienenitrile, 2,9-tridecadienenitrile, 2,9-tetradecadienenitrile, 2,9-pentadecadienenitrile, and 2,9-pentadecadienenitrile; the isomers of 2,10-alkadienenitrile are selected from the group consisting of isomers of 2,10-undecadienenitrile, 2,10-dodecadienenitrile, 2,10-tridecadienenitrile, 2,10-tetradecadienenitrile, and 2,10-pentadecadienenitrile; the isomers of 2,11-alkadienenitrile are selected from the group consisting of isomers of 2,11-dodecadienenitrile, 2,11-tridecadienenitrile, 2,11-tetradecadienenitrile, and 2,11-pentadecadienenitrile; the isomers of 2,12-alkadienenitrile are selected from the group consisting of isomers of 2,12-tridecadienenitrile, 2,12-tetradecadienenitrile, and 2,12-pentadecadienenitrile; the isomers of 2,13-alkadienenitrile are selected from the group consisting of the isomers of 2,13-tetradecadienenitrile and 2,13-pentadecadienenitrile; and the isomers of 2,14-alkadienenitrile are selected from the isomers of 2,14-pentadecadienenitrile.

10. The composition of clause 1, the fragrance or flavor composition of clause 2, and the method of clause 3, wherein the at least one isomeric alkadienal is selected from the group consisting of E,Z-2,6-octadienal, E,Z-2,7-nonadienal, E,Z-2,6-decadienal, E,Z-2,7-decadienal, E,Z-2,7-undecadienal, E,Z-2,8-undecadienal, E,Z-2,10-tridecadienal, E,Z-2,7-tetradecadienal, E,Z-2,11-tetradecadienal, 5-methyl-E,Z-2,7-nonadienal, and 5-methyl-E,Z-2,7-decadienal.

11. The composition of clause 1, the fragrance or flavor composition of clause 2, and the method of clause 3, wherein the at least one isomeric alkadienenitrile is selected from the group consisting of E,Z-2,6-octadienenitrile, E,Z-2,7-nonadienenitrile, E,Z-2,7-decadienenitrile, E,Z-2,8-decadienenitrile, E,Z-2,8-undecadienenitrile, E,Z-2,9-dodecadienenitrile, E,Z-2,10-tridecadienenitrile, and E,Z-2,11-tetradecadienenitrile.

12. The composition of clause 1, the fragrance or flavor composition of clause 2, and the method of clause 3, wherein the at least one isomeric alkadienal is represented by the formula

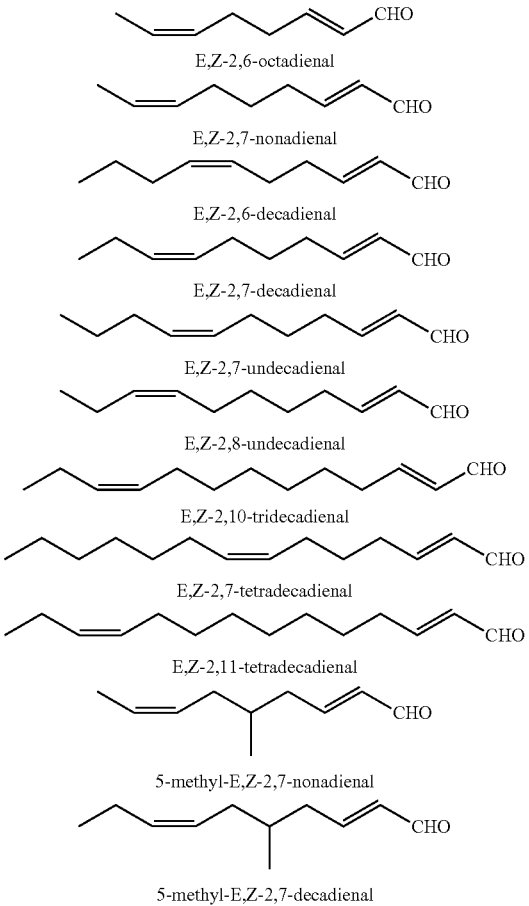

13. The composition of clause 1, the fragrance or flavor composition of clause 2, and the method of clause 3, wherein the at least one isomeric alkadienenitrile is represented by the formula

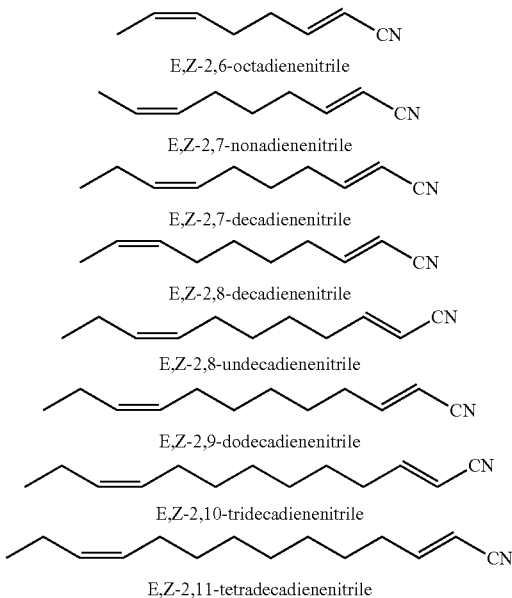

E,Z-2,6-octadienenitrile
E,Z-2,7-nonadienenitrile
E,Z-2,7-decadienenitrile
E,Z-2,8-decadienenitrile
E,Z-2,8-undecadienenitrile
E,Z-2,9-dodecadienenitrile
E,Z-2,10-tridecadienenitrile
E,Z-2,11-tetradecadienenitrile 14. The composition of clause 1, the fragrance or flavor composition of clause 2, and the method of clause 3, wherein the at least one isomeric alkadienal or the at least one isomeric alkadienenitrile is present in an amount of at least about 1 ppm by weight, based on the total weight of the composition, to impart a fragrance to the composition or the consumer product.

15. The composition of clause 1, the fragrance or flavor composition of clause 2, and the method of clause 3, wherein the at least one isomeric alkadienal or the at least one isomeric alkadienenitrile is present in an amount of at least about 0.1 ppm by weight, based on the total weight of the composition, to impart a flavor to the composition or the consumer product.

16. The composition of clause 1, the fragrance or flavor composition of clause 2, and the method of clause 3, wherein the at least one isomeric alkadienal or the at least one isomeric alkadienenitrile is combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropyl-phenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-01, phenoxyethylisobutyrate, phenylacetaldehydedimethylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition or the consumer product.

17. The composition of clause 1, the fragrance or flavor composition of clause 2, and the method of clause 3, wherein the at least one isomeric alkadienal or the at least one isomeric alkadienenitrile is combined with geraniol, geranyl acetate, linalool, linalyl acetate, citronellol, citronellyl acetate, terpineol, terpinyl acetate, 2-phenylethanol, 2-phenylethyl acetate, benzyl alcohol, benzyl acetate, benzyl salicylate, heliotropine, benzaldehyde, anisaldehyde, benzyl salicylate, e, n-decanal, n-dodecanal, 9-decen-1-01, coumarin, eugenol, vanillin, hexanal, eucalyptol, ionones, methylionones, isomethylionones, irones, cis-3-hexenol and esters of the latter, acetaldehyde, ethyl acetate, ethyl butyratecinnamic aldehyde, cuminic aldehyde, furfural, cinnamic aldehyde, maltol, ethyl maltol, dimethyl sulfide, gamma decalactone, gamma undecalactone, diacetyl, ethyl valerate, damascone, damascenone, methyl caproate, cyclotene, butyric acid, acetoin, delta decalactone, furaneol, acetoin, benzodihydro pyrone, 2,6-nonadienal, melonal or methyl heptane carbonate, to impart a flavor to the composition or the consumer product.

18. A consumer product containing the fragrance or flavor composition of clause 2.

19. The consumer product of clause 18 selected from the group consisting of a candle, an air care product, a perfume, a cologne, a soap, a personal care product, a detergent, a fabric care product, and a household cleaning product.

20. The consumer product of clause 18 selected from the group consisting of a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

21. The consumer product of clause 18 selected from the group consisting of an air care product, a perfume, and a cologne.

22. The consumer product of clause 18 selected from the group consisting of a beverage, a powder or semi-frozen/frozen concentrate for a drink, a candy, a sugarless candy, a chocolate, a chewing gum, a bubble gum, a condiment, a spice, a seasoning, a dry cereal, an oatmeal, a granola bar, an alcoholic beverage, an energy beverage, a juice, a tea, a coffee, a salsa, a gel bead, a film strip for halitosis, a lozenge, a cough drop, a throat lozenge, a throat spray, a toothpaste, and a mouth rinse.

23. The consumer product of clause 18 selected from the group consisting of a beverage, a dairy product, a confectionary, a cereal, a snack, and a soup.

24. The consumer product of clause 18 selected from the group consisting of a beverage, a chewing gum, and a bubble gum.

25. The method of clause 18 wherein the consumer product is selected from the group consisting of a candle, an air care product, a perfume, a cologne, a soap, a personal care product, a detergent, a fabric care product, and a household cleaning product.

26. The method of clause 3 wherein the consumer product is selected from the group consisting of a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

27. The method of clause 3 wherein the consumer product is selected from the group consisting of an air care product, a perfume, and a cologne.

28. The method of clause 3 wherein the consumer product is selected from the group consisting of a beverage, a powder or semi-frozen/frozen concentrate for a drink, a candy, a sugarless candy, a chocolate, a chewing gum, a bubble gum, a condiment, a spice, a seasoning, a dry cereal, an oatmeal, a granola bar, an alcoholic beverage, an energy beverage, a juice, a tea, a coffee, a salsa, a gel bead, a film strip for halitosis, a lozenge, a cough drop, a throat lozenge, a throat spray, a toothpaste, and a mouth rinse.

29. The method of clause 3 wherein the consumer product is selected from the group consisting of a beverage, a dairy product, a confectionary, a cereal, a snack, and a soup.

30. The method of clause 3 wherein the consumer product is selected from the group consisting of a beverage, a chewing gum, and a bubble gum.

The quantities in which the compositions of this disclosure can be used in flavor compositions or in products to be flavored can vary within wide limits and depend inter alia on the nature of the product in which the flavor material is used, on the nature and quantity of the other components in the composition and on the organoleptic effect which is aimed at. It is therefore only possible to specify very rough limits, which, however, provide sufficient information for the specialist to be able to use the compounds according to the disclosure independently. In most cases a quantity of only 1 ppm in a flavor composition will already be sufficient to obtain a clearly perceptible taste effect. On the other hand, to achieve special organoleptic effects it is possible to use quantities of 10, 100, 500 ppm or even more in a composition.

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

The following examples are only to illustrate the preparation and use of the compounds according to the disclosure. The disclosure is not limited thereto.

Example 1

Preparation of E,Z-2,7-Decadienal

Cis-5-octenal 15.1 g (120 mmol) is fed to a catalytic amount of PTSA dissolved in anhydrous ethanol (1.5 g) and 17.8 g triethylorthoformate (120 mmol), maintaining a temperature below 20° C. Once the diethyl acetal formation is complete, the reaction mixture is neutralized with a 25% solution of sodium methoxide in methanol and then the lights are stripped atmospherically to 100° C.

10 g of Cis-5-octenal diethyl acetal (50 mmol) is added to a nitrogen purged flask and a catalytic amount of boron trifluoride diethyl etherate is added followed by a mixed feed of 10 g cis-5-octenal DEA (50 mmol) and 3 g ethyl vinyl ether (42 mmol) keeping the reaction temperature between 30-40° C. The reaction is quenched with 10% sodium hydroxide solution then the organic layer is washed with water. The unreacted diethyl acetal is separated from the 8,10,10-triethoxy-3Z-decene. The purified triethoxy is then reacted with 8 equivalents of formic acid to give a product consisting of E,Z-2,7-decadienal (96.23%). The remainder being the minor quantities of E,E-, Z,Z-, and Z,E isomers (combined 3.77%).

Example 2

Preparation of E,Z-2,11-Tetradecadienal

Cis-9-dodecenal 22.1 g (120 mmol) is fed to a catalytic amount of PTSA dissolved in anhydrous ethanol (1.5 g) and 17.8 g triethylorthoformate (120 mmol), maintaining a temperature below 20° C. Once the diethyl acetal formation is complete, the reaction mixture is neutralized with a 25% solution of sodium methoxide in methanol and then the lights are stripped atmospherically to 100° C.

12.8 g of Cis-9-dodecenal diethyl acetal (50 mmol) is added to a nitrogen purged flask and a catalytic amount of boron trifluoride diethyl etherate is added followed by a mixed feed of 12.8 g cis-9-dodecenal DEA (50 mmol) and 3 g ethyl vinyl ether (42 mmol) keeping the reaction temperature between 30-40° C. The reaction is quenched with 10% sodium hydroxide solution then the organic layer is washed with water. The unreacted diethyl acetal is separated from the 12,14,14-triethoxy-3Z-tetradecene. The purified triethoxy is then reacted with 8 equivalents of formic acid to give a product consisting of E,Z-2,11-tetradecadienal (~96%). The remainder being the minor quantities of E,E-, Z,Z-, and Z,E isomers (combined ~4%). BP is 75° C. at 0.1 mm.

Example 3

Preparation of E,Z-2,6-Octadienal

Cis-4-hexenal 11.8 g (120 mmol) is fed to a catalytic amount of PTSA dissolved in anhydrous ethanol (1 g) and 17.8 g triethylorthoformate (120 mmol), maintaining a temperature below 20° C. Once the diethyl acetal formation is complete, the reaction mixture is neutralized with a 25% solution of sodium methoxide in methanol and then the lights are stripped atmospherically to 100° C.

8.6 g of Cis-4-hexenal diethyl acetal (50 mmol) is added to a nitrogen purged flask and a catalytic amount of boron trifluoride diethyl etherate is added followed by a mixed feed of 8.6 g cis-4-hexenal DEA (50 mmol) and 3 g ethyl vinyl ether (42 mmol) keeping the reaction temperature between 30-40° C. The reaction is quenched with 10% sodium hydroxide solution then the organic layer is washed with water. The unreacted diethyl acetal is separated from the 6,8,8-triethoxy-2Z-octadecene. The purified triethoxy is then reacted with 8 equivalents of formic acid to give a product consisting of E,Z-2,6-octadienal (92.3%). The remainder being the minor quantities of E,E-Z,Z- and Z,E isomers (combined 7.7%). BP is 55° C. at 0.1 mm.

Example 4

Fragrance Formulation Containing E,Z-2,7-Decadienal

Perfume compositions belonging to the olfactive family green floral was formulated using E,Z-2,7-decadienal in an appropriate quantity to provide a fresh, green, ozonic, floral odor emphasizing iris notes.

| Green Floral Perfume | |
|---|---|
| Benzyl Acetate | 5 |
| Cymene para | 0.3 |
| Dihydro Ionone Beta | 24.5 |

-continued

| Green Floral Perfume | |
| --- | --- |
| DPG | 16 |
| Eucalyptol | 1 |
| Ionone Beta | 112 |
| Coranol | 295 |
| Myrcene | 0.5 |
| Orange Terpenes | 3 |
| Pinene Alpha | 0.2 |
| Pinene Beta | 1 |
| Rose Oxide | 1 |
| Terpineol Alpha | 540 |
| E,Z-2,7-Decadienal | 0.5 |
| Total | 1000 |

Example 5

Fragrance Formulation Containing E,Z-2,10-Tridecadienal

Perfume compositions imparting fresh citrus floral effect are created using E,Z-2,10-tridecadienal in an appropriate quantity.

| Soft, fresh, floral fragrance | |
| --- | --- |
| Apritone | 10 |
| Methoxy Melonal BRI 280 10% | 7 |
| Florol | 30 |
| Hedione | 100 |
| Dimeth Phen Eth Carbinol | 100 |
| Hydroxy Citronellol | 400 |
| DPG | 253 |
| Lilytol BRI 660 | 70 |
| Vionil BRI 640 1% | 10 |
| 3,6-Nonadienol BRI 330 1% | 10 |
| E,Z-2,10-Tridecadienal | 10 |
| Total | 1000 |

Example 6

Watermelon Flavor Composition Containing E,Z-2,7- and E,Z-2,8-Undecadienals

A watermelon flavor formulation was prepared having the following ingredients:

| Watermelon flavor formulation: | |
| --- | --- |
| Ethyl Maltol | 0.60 |
| Cis-3-Hexenol 1% | 0.15 |
| 2,6-Nonadienal 10% | 0.10 |
| Trans-2-Hexenal 10% | 0.10 |
| Benzaldehyde | 0.10 |
| Ethyl Acetate | 1.50 |
| Ethyl Butyrate | 2.30 |
| Melonal | 1.40 |
| Alpha Ionone | 0.45 |
| Methyl Heptine Carbonate 10% | 0.60 |
| Propylene Glycol | 92.70 |
| Total | 100.00 |

Flavored water for the test was prepared by adding 200 ppm sucralose 25% solution and 50 ppm of the above formulated watermelon flavor followed by the addition of 0.1 ppm each of E,Z-2,7-undecadienal and E,Z-2,8-undecadienal. The formulation with these two alkadienals of the disclosure was then compared with the same formulation without them by an expert panel. The flavored water containing the watermelon with two alkadienals was unanimously preferred for having a fresh and sweet watermelon aroma and taste missing in the base solution without alkadienals.

Example 7

Caramel Flavor Composition Containing E,Z-2,11-Tetradecadienal

A caramel flavor formulation was prepared having the following ingredients:

| Caramel formulation | |
| --- | --- |
| Vanillin | 5.00 |
| Maltol | 1.50 |
| Cyclotene | 0.75 |
| Ethyl Maltol | 2.50 |
| Diacetyl | 0.05 |
| Butyric Acid | 0.50 |
| Acetoin | 1.50 |
| Delta Decalactone | 0.10 |
| Gamma Decalactone | 0.50 |
| Ethyl Butyrate | 0.25 |
| Propylene Glycol | 87.35 |
| Total | 100.00 |

Flavored milk for the test was prepared by adding 300 ppm sucralose 25% solution, 0.05% of the above formulated caramel flavor followed by 4 ppm of E,Z-2,11-tetradecadienal. The formulation containing E,Z-2,11-tetradecadienal was compared with the same formulation without the alkadienal by an expert panel. The flavored milk containing the caramel flavor with E,Z-2,11-tetradecadienal was overwhelmingly preferred for having a rich creamy caramel taste missing in the base solution without the alkadienal of the disclosure.

Example 8

Bakery Flavor Composition Containing E,Z-2,6-Octadienal

A bakery flavor formulation was prepared having the following ingredients:

| Graham Cracker formulation | |
| --- | --- |
| Ethone | 0.50 |
| Vanillin | 5.00 |
| Maltol | 1.00 |
| Furaneol | 0.50 |
| Cyclotene | 0.20 |
| Acetoin | 1.00 |
| Aldehyde C-18 (Gamma Nonalactone) | 0.05 |
| Heliotropin | 0.05 |
| Benzodihydro Pyrone | 0.05 |
| Propylene Glycol | 91.65 |
| Total | 100.00 |

Flavored milk was prepared by adding 300 ppm of sucralose 25% solution followed by 0.05% Graham Cracker flavor and 0.02 ppm of E,Z-2,6-octadienal. The formulation with and without the alkadienal was tested by an expert panel. The flavored milk containing E,Z-2,6-octadienal was unanimously preferred over the sample without.

Example 9

Preparation of E,Z-Decadienenitrile and its Isomers 35.1 g of cis-5-octenal (198 mmol) is mixed with 25 g of diethyl cyanomethylphosphonate (198 mmol) and 24.5 g of a 45% solution of potassium hydroxide in water is fed maintaining a temperature of 20-25° C. Once the reaction is complete, 10 g of cyclohexane is added and the solution is washed with water, acidified with a 5% aqueous solution of citric acid, then neutralized with a 5% aqueous solution of sodium carbonate prior to distillation. The crude isomeric ratio is about 69% E,Z to 31% E,E. The isomeric content can be enriched via distillation.

Example 10

Fragrance Formulation Containing E,Z-2,7-Decadienenitrile

A green, fruity, floral, woody fragrance formulation was prepared having the following ingredients:

| | |
|---|---|
| Ald C-10 10% | 15 |
| Benz Acetate | 5 |
| Cymene-para 10% | 3 |
| Dihydro Ionone Beta | 24 |
| Eucalyptol | 1 |
| Ionone Beta | 112 |
| Coranol | 295 |
| Myrcene 10% | 5 |
| Orange Terpenes | 3 |
| Limedien 1% | 2 |
| Rose Oxide | 1 |
| Terpineol alpha | 500 |
| E,Z-2,7-Decadienenitrile 1% DPG | 20 |
| DPG (diporopylene glycol) | 14 |
| Total | 1000 |

The present disclosure is not to be limited in scope by the specific embodiments described herein. Indeed, various modifications of the disclosure in addition to those described herein will become apparent to those skilled in the art from the foregoing description. Such modifications are intended to fall within the scope of the appended claims.

What is claimed is:

1. A composition comprising at least one isomeric alkadienal or at least one isomeric alkadienenitrile in an amount effective to impart a fragrance or flavor to the composition; wherein the at least one isomeric alkadienal or the at least one isomeric alkadienenitrile has from about 0.1 weight percent to about 99.5 weight percent of E,Z isomers, from about 0.1 weight percent to about 99.5 weight percent of Z,E isomers, from about 0.1 weight percent to about 99.5 weight percent of E,E isomers, and from about 0.1 weight percent to about 99.5 weight percent of Z,Z isomers, based on the total Z and E isomers in the composition.

2. The composition of claim 1 wherein the at least one isomeric alkadienal or the at least one isomeric alkadienenitrile has from about 10 percent to about 98 percent of E,Z isomers, from about 0.5 percent to about 40 percent of Z,E isomers, from about 0.1 percent to about 40 percent of E,E isomers, and from about 2 percent to about 40 percent of Z,Z isomers, based on the total Z and E isomers in the composition.

3. The composition of claim 1 wherein the at least one isomeric alkadienal is selected from the group consisting of isomers of 2,6-alkadienal, 2,7-alkadienal, 2,8-alkadienal, 2,9-alkadienal, 2,10-alkadienal, 2,11-alkadienal, 2,12-alkadienal, 2,13-alkadienal, and 2,14-alkadienal.

4. The composition of claim 1 wherein the at least one isomeric alkadienenitrile is selected from the group consisting of isomers of 2,6-alkadienenitrile, 2,7-alkadienenitrile, 2,8-alkadienenitrile, 2,9-alkadienenitrile, 2,10-alkadienenitrile, 2,11-alkadienenitrile, 2,12-alkadienenitrile, 2,13-alkadienenitrile, and 2,14-alkadienenitrile.

5. The composition of claim 3 wherein the isomers of 2,6-alkadienal are selected from the group consisting of isomers of 2,6-heptadienal, 2,6-octadienal, 2,6-nonadienal, 2,6-decadienal, 2,6-undecadienal, 2,6-dodecadienal, 2,6-tridecadienal, 2,6-tetradecadienal, and 2,6-pentadecadienal; the isomers of 2,7-alkadienal are selected from the group consisting of isomers of 2,7-octadienal, 2,7-nonadienal, 2,7-decadienal, 2,7-undecadienal, 2,7-dodecadienal, 2,7-tridecadienal, 2,7-tetradecadienal, and 2,7-pentadecadienal; the isomers of 2,8-alkadienal are selected from the group consisting of isomers of 2,8-nonadienal, 2,8-decadienal, 2,8-undecadienal, 2,8-dodecadienal, 2,8-tridecadienal, 2,8-tetradecadienal, and 2,8-pentadecadienal; the isomers of 2,9-alkadienal are selected from the group consisting of isomers of 2,9-decadienal, 2,9-undecadienal, 2,9-dodecadienal, 2,9-tridecadienal, 2,9-tetradecadienal, and 2,9-pentadecadienal; the isomers of 2,10-alkadienal are selected from the group consisting of isomers of 2,10-undecadienal, 2,10-dodecadienal, 2,10-tridecadienal, 2,10-tetradecadienal, and 2,10-pentadecadienal; the isomers of 2,11-alkadienal are selected from the group consisting of isomers of 2,11-dodecadienal, 2,11-tridecadienal, 2,11-tetradecadienal, and 2,11-pentadecadienal; the isomers of 2,12-alkadienal are selected from the group consisting of isomers of 2,12-tridecadienal, 2,12-tetradecadienal, and 2,12-pentadecadienal; the isomers of 2,13-alkadienal are selected from the group consisting of the isomers of 2,13-tetradecadienal and 2,13-pentadecadienal; and the isomers of 2,14-alkadienal are selected from isomers of 2,14-pentadecadienal.

6. The composition of claim 4 wherein the isomers of 2,6-alkadienenitrile are selected from the group consisting of isomers of 2,6-heptadienenitrile, 2,6-octadienenitrile, 2,6-nonadienenitrile, 2,6-decadienenitrile, 2,6-undecadienenitrile, 2,6-dodecadienenitrile, 2,6-tridecadienenitrile, 2,6-tetradecadienenitrile, and 2,6-pentadecadienenitrile; the isomers of 2,7-alkadienenitrile are selected from the group consisting of isomers of 2,7-octadienenitrile, 2,7-nonadienenitrile, 2,7-decadienenitrile, 2,7-undecadienenitrile, 2,7-dodecadienenitrile, 2,7-tridecadienenitrile, 2,7-tetradecadienenitrile, and 2,7-pentadecadienenitrile; the isomers of 2,8-alkadienenitrile are selected from the group consisting of isomers of 2,8-nonadienenitrile, 2,8-decadienenitrile, 2,8-undecadienenitrile, 2,8-dodecadienenitrile, 2,8-tridecadienenitrile, 2,8-tetradecadienenitrile, and 2,8-pentadecadienenitrile; the isomers of 2,9-alkadienenitrile are selected from the group consisting of isomers of 2,9-decadienenitrile, 2,9-undecadienenitrile, 2,9-dodecadienenitrile, 2,9-tridecadienenitrile, 2,9-tetradecadienenitrile, 2,9-pentadecadienenitrile, and 2,9-pentadecadienenitrile; the isomers of 2,10-alkadienenitrile are selected from the group consisting of isomers of 2,10-undecadienenitrile, 2,10-dodecadienenitrile, 2,10-tridecadienenitrile, 2,10-tetradecadienenitrile, and 2,10-pentadecadienenitrile; the isomers of 2,11-alkadienenitrile are selected from the group consisting of isomers of 2,11-dodecadienenitrile, 2,11-tridecadienenitrile, 2,11-tetradecadienenitrile, and 2,11-pentadecadienenitrile; the isomers of 2,12-alkadienenitrile are selected from the group consisting of isomers of 2,12-tridecadienenitrile, 2,12-tetradecadienenitrile, and 2,12-pentadecadienenitrile; the isomers of 2,13-alkadienenitrile are selected from the group consisting of the isomers of 2,13-tetradecadienenitrile and 2,13-pentadecadienenitrile; and the isomers of 2,14-alkadienenitrile are selected from the isomers of 2,14-pentadecadienenitrile.

7. The composition of claim 1 wherein the at least one isomeric alkadienal is selected from the group consisting of E,Z-2,6-octadienal, E,Z-2,7-nonadienal, E,Z-2,6-decadienal, E,Z-2,7-decadienal, E,Z-2,7-undecadienal, E,Z-2,8-undecadienal, E,Z-2,10-tridecadienal, E,Z-2,7-tetradecadienal, E,Z-2,11-tetradecadienal, 5-methyl-E,Z-2,7-nonadienal, and 5-methyl-E,Z-2,7-decadienal.

8. The composition of claim 1 wherein the at least one isomeric alkadienenitrile is selected from the group consisting of E,Z-2,6-octadienenitrile, E,Z-2,7-nonadienenitrile, E,Z-2,7-decadienenitrile, E,Z-2,8-decadienenitrile, E,Z-2,8-undecadienenitrile, E,Z-2,9-dodecadienenitrile, E,Z-2,10-tridecadienenitrile, and E,Z-2,11-tetradecadienenitrile.

9. The composition of claim 1 wherein the at least one isomeric alkadienal is represented by the formula

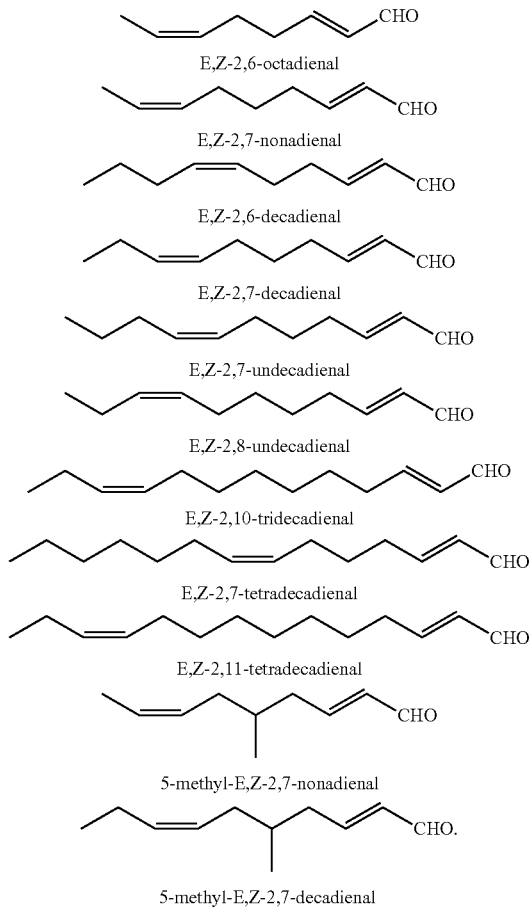

10. The composition of claim 1 wherein the at least one isomeric alkadienenitrile is represented by the formula

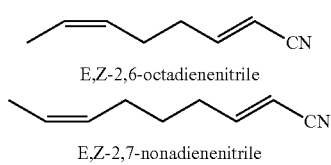

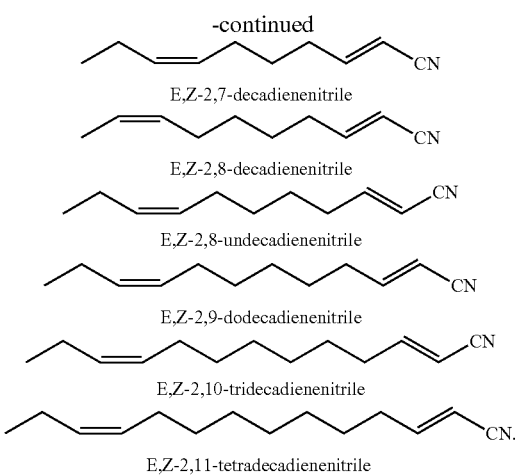

11. The composition of claim 1 wherein the at least one isomeric alkadienal or the at least one isomeric alkadienenitrile is present in an amount of at least about 1 ppm by weight, based on the total weight of the composition, to impart a fragrance to the composition.

12. The composition of claim 1 wherein the at least one isomeric alkadienal or the at least one isomeric alkadienenitrile is present in an amount of at least about 0.1 ppm by weight, based on the total weight of the composition, to impart a flavor to the composition.

13. The composition of claim 1 wherein the at least one isomeric alkadienal or the at least one isomeric alkadienenitrile is combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

14. The composition of claim 1 wherein the at least one isomeric alkadienal or the at least one isomeric alkadienenitrile is combined with geraniol, geranyl acetate, linalool, linalyl acetate, citronellol, citronellyl acetate, terpineol, terpinyl acetate, 2-phenylethanol, 2-phenylethyl acetate, benzyl alcohol, benzyl acetate, benzyl salicylate, heliotropine, benzaldehyde, anisaldehyde, benzyl salicylate, e, n-decanal, n-dodecanal, 9-decen-1-01, coumarin, eugenol, vanillin, hexanal, eucalyptol, ionones, methylionones, isomethylionones, irones, cis-3-hexenol and esters of the latter, acetaldehyde, ethyl acetate, ethyl butyratecinnamic aldehyde, cuminic aldehyde, furfural, cinnamic aldehyde, maltol, ethyl maltol, dimethyl sulfide, gamma decalactone, gamma undecalactone, diacetyl, ethyl valerate, damascone, damascenone, methyl caproate, cyclotene, butyric acid, acetoin, delta decalactone, furaneol, acetoin, benzodihydro pyrone, 2,6-nonadienal, melonal or methyl heptane carbonate, to impart a flavor to the composition.

15. A fragrance or flavor composition comprising at least one isomeric alkadienal or at least one isomeric alkadienenitrile in an amount effective to impart a fragrance or flavor to the composition; wherein the at least one isomeric alkadienal or the at least one isomeric alkadienenitrile has from about 0.1 weight percent to about 99.5 weight percent of E,Z isomers, from about 0.1 weight percent to about 99.5 weight percent of Z,E isomers, from about 0.1 weight percent to about 99.5 weight percent of E,E isomers, and from about 0.1 weight percent to about 99.5 weight percent of Z,Z isomers, based on the total Z and E isomers in the composition.

16. A consumer product containing the fragrance or flavor composition of claim 15.

17. The consumer product of claim 16 selected from the group consisting of a candle, an air care product, a perfume, a cologne, a soap, a personal care product, a detergent, a fabric care product, and a household cleaning product.

18. The consumer product of claim 16 selected from the group consisting of a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

19. A method of imparting a fragrance or flavor to a consumer product comprising adding to the consumer product a fragrance or flavor composition comprising at least one isomeric alkadienal or at least one isomeric alkadienenitrile in an amount effective to impart a fragrance or flavor to the consumer product; wherein the at least one isomeric alkadienal or the at least one isomeric alkadienenitrile has from about 0.1 weight percent to about 99.5 weight percent of E,Z isomers, from about 0.1 weight percent to about 99.5 weight percent of Z,E isomers, from about 0.1 weight percent to about 99.5 weight percent of E,E isomers, and from about 0.1 weight percent to about 99.5 weight percent of Z,Z isomers, based on the total Z and E isomers in the composition.

\* \* \* \* \*